United States Patent [19]

Ayer

[11] 4,226,984
[45] Oct. 7, 1980

[54] 2-DECARBOXY-2-AMINOMETHYL-TRANS-4,5-DIDEHYDRO-PGI₁ COMPOUNDS

[75] Inventor: Donald E. Ayer, Kalamazoo, Mich.

[73] Assignee: The Upjohn Company, Kalamazoo, Mich.

[21] Appl. No.: 938,547

[22] Filed: Aug. 31, 1978

Related U.S. Application Data

[63] Continuation-in-part of Ser. No. 821,542, Aug. 3, 1977.

[51] Int. Cl.² .................................................. C07D 307/93
[52] U.S. Cl. ............................... 542/426; 260/346.73; 542/429
[58] Field of Search ................... 260/346.73; 542/426, 542/429

[56] References Cited

PUBLICATIONS

Johnson et al., Prostaglandins, 12 (1976) p. 915.

Primary Examiner—Arthur P. Demers
Attorney, Agent, or Firm—Robert A. Armitage

[57] ABSTRACT

The present invention relates to certain structural and pharmacological analogs of prostacyclin (PGI₂) which are 2-Decarboxy-2-aminomethyl-trans-4,5-didehydro-PGI₁ compounds. These novel pharmacological agents are useful as smooth muscle stimulators.

82 Claims, No Drawings

2-DECARBOXY-2-AMINOMETHYL-TRANS-4,5-DIDEHYDRO-PGI₁ COMPOUNDS

CROSS REFERENCE TO RELATED APPLICATIONS

The present application is a continuation-in-part of Serial No. 821,542, filed Aug. 3, 1977, now U.S. Pat. No. 4,154,676.

The present invention relates to novel 2-decarboxy-2-aminomethyl-trans-4,5-didehydro-PGI$_1$ compounds, the essential material constituting a disclosure of the preparation and use thereof is incorporated here by reference from U.S. Pat. No. 4,109,082, issued Aug. 22, 1978.

The present invention particularly relates to the following compounds:

2-Decarboxy-2-aminomethyl-(6RS)-trans-4,5-didehydro-PGI$_1$;
2-Decarboxy-2-aminomethyl-trans-4,5-didehydro-6α-PGI$_1$;
2-Decarboxy-2-aminomethyl-15-methyl-trans-4,5-didehydro-6α-PGI$_1$;
2-Decarboxy-2-aminomethyl-16,16-dimethyl-trans-4,5-didehydro-6α-PGI$_1$;
2-Decarboxy-2-aminomethyl-16,16-difluoro-trans-4,5-didehydro-6α-PGI$_1$;
2-Decarboxy-2-aminomethyl-2,2-difluoro-trans-4,5-didehydro-6β-PGI$_1$;
2-Decarboxy-2-aminomethyl-17-phenyl-18,19,20-trinor-trans-4,5-didehydro-6β-PGI$_1$;
2-Decarboxy-2-aminomethyl-16-phenoxy-17,18,19,20-tetranor-trans-4,5-didehydro-6β-PGI$_1$;
2-Decarboxy-2-aminomethyl-15-methyl-trans-4,5-didehydro-6β-PGI$_1$;
2-Decarboxy-2-aminomethyl-16,16-difluoro-trans-4,5-didehydro-6β-PGI$_1$;
2-Decarboxy-2-aminomethyl-16,16-dimethyl-trans-4,5-didehydro-6β-PGI$_1$;
2-Decarboxy-2-aminomethyl-trans-4,5-didehydro-6β-PGI$_1$;
2-Decarboxy-2-aminomethyl-6(RS)-trans-4,5-didehydro-cis-13-PGI$_1$;
2-Decarboxy-2-aminomethyl-trans-4,5-didehydro-cis-13,6α-PGI$_1$;
2-Decarboxy-2-aminomethyl-15-methyl-trans-4,5-didehydro-cis-13-6α-PGI$_1$;
2-Decarboxy-2-aminomethyl-16,16-dimethyl-trans-4,5-didehydro-cis-13-6α-PGI$_1$;
2-Decarboxy-2-aminomethyl-16,16-difluoro-trans-4,5-didehydro-cis-13-6α-PGI$_1$;
2-Decarboxy-2-aminomethyl-2,2-difluoro-trans-4,5-didehydro-cis-13-6β-PGI$_1$;
2-Decarboxy-2-aminomethyl-17-phenyl-18,19,20-trinor-trans-4,5-didehydro-cis-13-6β-PGI$_1$;
2-Decarboxy-2-aminomethyl-16-phenoxy-17,18,19,20-tetranor-trans-4,5-didehydro-cis-13-6β-PGI$_1$;
2-Decarboxy-2-aminomethyl-15-methyl-trans-4,5-didehydro-cis-13-6β-PGI$_1$;
2-Decarboxy-2-aminomethyl-16,16-difluoro-trans-4,5-didehydro-cis-13-6β-PGI$_1$;
2-Decarboxy-2-aminomethyl-16,16-dimethyl-trans-4,5-didehydro-cis-13-6β-PGI$_1$;
2-Decarboxy-2-aminomethyl-trans-4,5-didehydro-cis-13-6β-PGI$_1$;
2-Decarboxy-2-aminomethyl-6(RS)-trans-4,5-didehydro-13,14-dihydro-PGI$_1$;
2-Decarboxy-2-aminomethyl-trans-4,5-didehydro-13,14-dihydro-6α-PGI$_1$;
2-Decarboxy-2-aminomethyl-15-methyl-trans-4,5-didehydro-13,14-dihydro-6α-PGI$_1$;
2-Decarboxy-2-aminomethyl-16,16-dimethyl-trans-4,5-didehydro-13,14-dihydro-6α-PGI$_1$;
2-Decarboxy-2-aminomethyl-16,16-difluoro-trans-4,5-didehydro-13,14-dihydro-6α-PGI$_1$;
2-Decarboxy-2-aminomethyl-2,2-difluoro-trans-4,5-didehydro-13,14-dihydro-6β-PGI$_1$;
2-Decarboxy-2-aminomethyl-17-phenyl-18,19,20-trinor-trans-4,5-didehydro-13,14-dihydro-6β-PGI$_1$;
2-Decarboxy-2-aminomethyl-16-phenoxy-17,18,19,20-tetranor-trans-4,5-didehydro-13,14-dihydro-6β-PGI$_1$;
2-Decarboxy-2-aminomethyl-15-methyl-trans-4,5-didehydro-13,14-dihydro-6β-PGI$_1$;
2-Decarboxy-2-aminomethyl-16,16-difluoro-trans-4,5-didehydro-13,14-dihydro-6β-PGI$_1$;
2-Decarboxy-2-aminomethyl-16,16-dimethyl-trans-4,5-didehydro-13,14-dihydro-6β-PGI$_1$; and
2-Decarboxy-2-aminomethyl-trans-4,5-didehydro-13,14-dihydro-6β-PGI$_1$.

I claim:
1. A prostacyclin analog of the formula

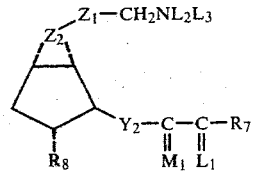

wherein Y$_2$ is trans—CH=CH—, cis—CH=CH—, or —CH$_2$CH$_2$—;
wherein Z$_2$ is

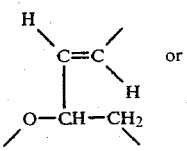 or (1)

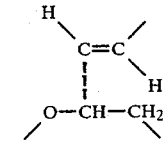 (2)

wherein Z$_1$ is
(1) —(CH$_2$)$_g$—CH$_2$—CH$_2$—, or
(2) —(CH$_2$)$_g$—CH$_2$—CF$_2$—,
wherein g is the integer zero, one, or 2;
wherein R$_8$ is hydrogen, hydroxy, or hydroxymethyl;
wherein M$_1$ is

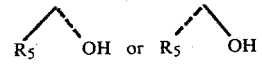

wherein R$_5$ is hydrogen or alkyl with one to 4 carbon atoms, inclusive; and
wherein L$_1$ is

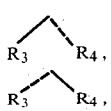

or a mixture of

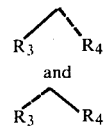

wherein $R_3$ and $R_4$ are hydrogen, methyl, or fluoro, being the same or different, with the proviso that one of $R_3$ and $R_4$ is fluoro only when the other is hydrogen or fluoro;

wherein $L_2$ and $L_3$ are hydrogen or alkyl of one to 4 carbon atoms, inclusive; and wherein $R_7$ is (1) $-(CH_2)_m-CH_3$,

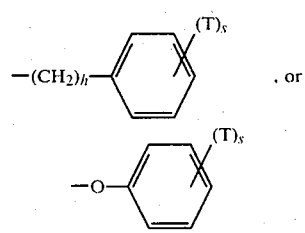

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Y_2$ is trans—CH=CH—.

3. A prostacyclin analog according to claim 2, wherein $Z_2$ is a mixture of

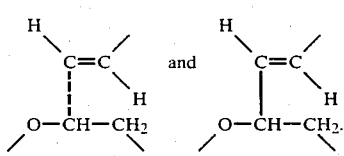

4. 2-Decarboxy-2-aminomethyl-(6RS)-trans-4,5-didehydro-PGI$_1$, a prostacyclin analog according to claim 3.

5. A prostacyclin analog according to claim 2, wherein $Z_2$ is

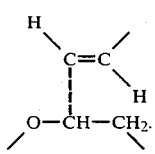

6. 2-Decarboxy-2-aminomethyl-trans-4,5-didehydro-6α-PGI$_1$, a prostacyclin analog according to claim 5.

7. 2-Decarboxy-2-aminomethyl-15-methyl-trans-4,5-didehydro-6α-PGI$_1$, a prostacyclin analog according to claim 5.

8. 2-Decarboxy-2-aminomethyl-16,16-dimethyl-trans-4,5-didehydro-6α-PGI$_1$, a prostacyclin analog according to claim 5.

9. 2-Decarboxy-2-aminomethyl-16,16-difluoro-trans-4,5-didehydro-6α-PGI$_1$, a prostacyclin analog according to claim 5.

10. A prostacyclin analog according to claim 2, wherein $Z_2$ is

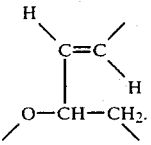

11. A prostacyclin analog according to claim 10, wherein $Z_1$ is $-(CH_2)_g-CH_2-CF_2-$.

12. 2-Decarboxy-2-aminomethyl-2,2-difluoro-trans-4,5-didehydro-6β-PGI$_1$, a prostacyclin analog according to claim 11.

13. A prostacyclin analog according to claim 10, wherein $Z_1$ is $-(CH_2)_g-CH_2-CH_2-$.

14. A prostacyclin analog according to claim 13, wherein g is zero.

15. A prostacyclin analog according to claim 14, wherein $R_7$ is

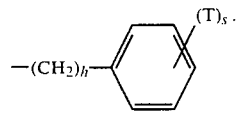

16. 2-Decarboxy-2-aminomethyl-17-phenyl-18,19,20-trinor-trans-4,5-didehydro-6β-PGI$_1$, a prostacyclin analog according to claim 15.

17. A prostacyclin analog according to claim 14, wherein $R_7$ is

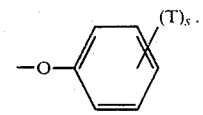

18. 2-Decarboxy-2-aminomethyl-16-phenoxy-17,18,19,20-tetranor-trans-4,5-didehydro-6β-PGI$_1$, a prostacyclin analog according to claim 17.

19. A prostacyclin analog according to claim 14, wherein $R_7$ is $-(CH_2)_m-CH_3-$.

20. A prostacyclin analog according to claim 19, wherein $R_5$ is methyl.

21. 2-Decarboxy-2-amino methyl-15-methyl-trans-4,5-didehydro-6β-PGI$_1$, a prostacyclin analog according to claim 20.

22. A prostacyclin analog according to claim 19, wherein $R_5$ is hydrogen.

23. A prostacyclin analog according to claim 22, wherein at least one of $R_3$ and $R_4$ is fluoro.

24. 2-Decarboxy-2-aminomethyl-16,16-difluoro-trans-4,5-didehydro-6β-PGI$_1$, a prostacyclin analog according to claim 23.

25. A prostacyclin analog according to claim 22, wherein at least one of $R_3$ and $R_4$ is methyl.

26. 2-Decarboxy-2-aminomethyl-16,16-dimethyl-trans-4,5-didehydro-6β-PGI₁, a prostacyclin analog according to claim 25.

27. A prostacyclin analog according to claim 22, wherein R₃ and R₄ are both hydrogen.

28. 2-Decarboxy-2-aminomethyl-trans-4,5-didehydro-6β-PGI₁, a prostacyclin analog according to claim 27.

29. A prostacyclin analog according to claim 1, wherein Y₂ is cis—CH=CH—.

30. A prostacyclin analog according to claim 29, wherein Z₂ is a mixture of

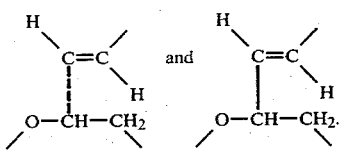

31. 2-Decarboxy-2-aminomethyl-6(RS)-trans-4,5-didehydro-cis-13-PGI₁, a prostacyclin analog according to claim 30.

32. A prostacyclin analog according to claim 29, wherein Z₂ is

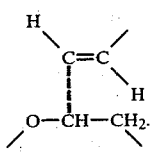

33. 2-Decarboxy-2-aminomethyl-trans-4,5-didehydro-cis-13-6α-PGI₁, a prostacyclin analog according to claim 32.

34. 2-Decarboxy-2-aminomethyl-15-methyl-trans-4,5-didehydro-cis-13-6α-PGI₁, a prostacyclin analog according to claim 32.

35. 2-Decarboxy-2-aminomethyl-16,16-dimethyl-trans-4,5-didehydro-cis-13-6β-PGI₁, a prostacyclin analog according to claim 32.

36. 2-Decarboxy-2-aminomethyl-16,16-difluoro-trans-4,5-didehydro-cis-13-6α-PGI₁, a prostacyclin analog according to claim 32.

37. A prostacyclin analog according to claim 29, wherein Z₂ is

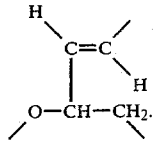

38. A prostacyclin analog according to claim 37, wherein Z₁ is —(CH₂)$_g$—CH₂—CF₂—.

39. 2-Decarboxy-2-aminomethyl-2,2-difluoro-trans-4,5-didehydro-cis-13-6β-PGI₁, a prostacyclin analog according to claim 38.

40. A prostacyclin analog according to claim 37, wherein Z₁ is —(CH₂)$_g$—CH₂—CH₂—.

41. A prostacyclin analog according to claim 40, wherein g is zero.

42. A prostacyclin analog according to claim 41, wherein R₇ is

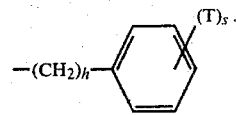

43. 2-Decarboxy-2-aminomethyl-17-phenyl-18,19,20-trinor-trans-4,5-didehydro-cis-13-6β-PGI₁, a prostacyclin analog according to claim 42.

44. A prostacyclin analog according to claim 41, wherein R₇ is

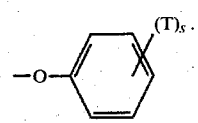

45. 2-Decarboxy-2-aminomethyl-16-phenoxy-17,18,19,20-tetranor-trans-4,5-didehydro-cis-13-6β-PGI₁, a prostacyclin analog according to claim 44.

46. A prostacyclin analog according to claim 41, wherein R₇ is —(CH₂)$_m$—CH₃—.

47. A prostacyclin analog according to claim 46, wherein R₅ is methyl.

48. 2-Decarboxy-2-aminomethyl-15-methyl-trans-4,5-didehydro-cis-13-6β-PGI₁, a prostacyclin analog according to claim 47.

49. A prostacyclin analog according to claim 46, wherein R₅ is hydrogen.

50. A prostacyclin analog according to claim 49, wherein at least one of R₃ and R₄ is fluoro.

51. 2-Decarboxy-2-aminomethyl-16,16-difluoro-trans-4,5-didehydro-cis-13-6β-PGI₁, a prostacyclin analog according to claim 50.

52. A prostacyclin analog according to claim 49, wherein at least one of R₃ and R₄ is methyl.

53. 2-Decarboxy-2-aminomethyl-16,16-dimethyl-trans-4,5-didehydro-cis-13-6β-PGI₁, a prostacyclin analog according to claim 52.

54. A prostacyclin analog according to claim 49, wherein R₃ and R₄ are both hydrogen.

55. 2-Decarboxy-2-aminomethyl-trans-4,5-didehydro-cis-13-6β-PGI₁, a prostacyclin analog according to claim 54.

56. A prostacyclin analog according to claim 1, wherein Y₂ is —CH₂CH₂—.

57. A prostacyclin analog according to claim 56, wherein Z₂ is a mixture of

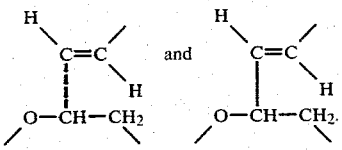

58. 2-Decarboxy-2-aminomethyl-6(RS)-trans-4,5-didehydro-13,14-dihydro-PGI₁, a prostacyclin analog according to claim 57.

59. A prostacyclin analog according to claim 56, wherein Z₂ is

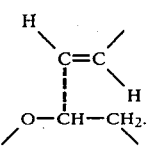

60. 2-Decarboxy-2-aminomethyl-trans-4,5-didehydro-13,14-dihydro-6α-PGI$_1$, a prostacyclin analog according to claim 59.

61. 2-Decarboxy-2-aminomethyl-15-methyl-trans-4,5-didehydro-13,14-dihydro-6α-PGI$_1$, a prostacyclin analog according to claim 59.

62. 2-Decarboxy-2-aminomethyl-16,16-dimethyl-trans-4,5-didehydro-13,14-dihydro-6α-PGI$_1$, a prostacyclin analog according to claim 59.

63. 2-Decarboxy-2-aminomethyl-16,16-difluoro-trans-4,5-didehydro-13,14-dihydro-6α-PGI$_1$, a prostacyclin analog according to claim 59.

64. A prostacyclin analog according to claim 56, wherein Z$_2$ is

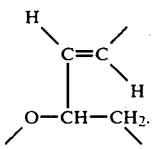

65. A prostacyclin analog according to claim 64, wherein Z$_1$ is —(CH$_2$)$_g$—CH$_2$—CF$_2$—.

66. 2-Decarboxy-2-aminomethyl-2,2-difluoro-trans-4,5-didehydro-13,14-dihydro-6β-PGI$_1$, a prostacyclin analog according to claim 65.

67. A prostacyclin analog according to claim 64, wherein Z$_1$ is —(CH$_2$)$_g$—CH$_2$—CH$_2$—.

68. A prostacyclin analog according to claim 67, wherein g is zero.

69. A prostacyclin analog according to claim 68, wherein R$_7$ is

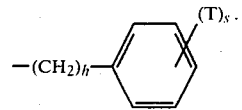

70. 2-Decarboxy-2-aminomethyl-17-phenyl-18,19,20-trinor-trans-4,5-didehydro-13,14-dihydro-6β-PGI$_1$, a prostacyclin analog according to claim 69.

71. A prostacyclin analog according to claim 68, wherein R$_7$ is

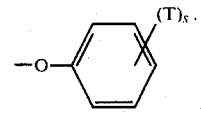

72. 2-Decarboxy-2-aminomethyl-16-phenoxy-17,18,19,20-tetranor-trans-4,5-didehydro-13,14-dihydro-6β-PGI$_1$, a prostacyclin analog according to claim 71.

73. A prostacyclin analog according to claim 68, wherein R$_7$ is —(CH$_2$)$_m$—CH$_3$—.

74. A prostacyclin analog according to claim 73, wherein R$_5$ is methyl.

75. 2-Decarboxy-2-aminomethyl-15-methyl-trans-4,5-didehydro-13,14-dihydro-6β-PGI$_1$, a prostacyclin analog according to claim 74.

76. A prostacyclin analog according to claim 73, wherein R$_5$ is hydrogen.

77. A prostacyclin analog according to claim 76, wherein at least one of R$_3$ and R$_4$ is fluoro.

78. 2-Decarboxy-2-aminomethyl-16,16-difluoro-trans-4,5-didehydro-13,14-dihydro-6β-PGI$_1$, a prostacyclin analog according to claim 77.

79. A prostacyclin analog according to claim 76, wherein at least one of R$_3$ and R$_4$ is methyl.

80. 2-Decarboxy-2-aminomethyl-16,16-dimethyl-trans-4,5-didehydro-13,14-dihydro-6β-PGI$_1$, a prostacyclin analog according to claim 79.

81. A prostacyclin analog according to claim 76, wherein R$_3$ and R$_4$ are both hydrogen.

82. 2-Decarboxy-2-aminomethyl-trans-4,5-didehydro-13,14-dihydro-6β-PGI$_1$, a prostacyclin analog according to claim 81.

* * * * *

UNITED STATES PATENT OFFICE
CERTIFICATE OF CORRECTION

Patent No. 4,226,984    Dated  7 October 1980

Inventor(s) Doald E. Ayer

It is certified that error appears in the above-identified patent and that said Letters Patent are hereby corrected as shown below:

Column 1, lines 9-10, delete reference to U.S. Pat. No. 4,154,676.

The portion of the term of this patent subsequent to May 13, 1997 has been disclaimed.

Signed and Sealed this

Twenty-fourth Day of March 1981

[SEAL]

*Attest:*

RENE D. TEGTMEYER

*Attesting Officer*    *Acting Commissioner of Patents and Trademarks*